(12) United States Patent
Miyama et al.

(10) Patent No.: US 12,246,112 B2
(45) Date of Patent: Mar. 11, 2025

(54) ARTIFICIAL BLOOD VESSEL

(71) Applicant: DENKA COMPANY LIMITED, Tokyo (JP)

(72) Inventors: Akira Miyama, Tokyo (JP); Mutsumi Matsumoto, Tokyo (JP)

(73) Assignee: DENKA COMPANY LIMITED, Tokyo (JP)

( * ) Notice: Subject to any disclaimer, the term of this patent is extended or adjusted under 35 U.S.C. 154(b) by 882 days.

(21) Appl. No.: 17/284,023

(22) PCT Filed: Oct. 25, 2019

(86) PCT No.: PCT/JP2019/041851
§ 371 (c)(1),
(2) Date: Apr. 9, 2021

(87) PCT Pub. No.: WO2020/095713
PCT Pub. Date: May 14, 2020

(65) Prior Publication Data
US 2021/0330865 A1    Oct. 28, 2021

(30) Foreign Application Priority Data
Nov. 8, 2018  (JP) .................. 2018-210480

(51) Int. Cl.
*A61L 27/50*       (2006.01)
*A61L 27/16*       (2006.01)
(Continued)

(52) U.S. Cl.
CPC ............. *A61L 27/507* (2013.01); *A61L 27/16* (2013.01); *A61L 27/34* (2013.01); *A61L 27/48* (2013.01);
(Continued)

(58) Field of Classification Search
CPC ............ A61F 2/06; A61L 27/16; A61L 27/34; A61L 27/48; A61L 27/507; B32B 1/08;
(Continued)

(56) References Cited

U.S. PATENT DOCUMENTS 5,904,967 A    5/1999  Ezaki et al.
8,580,884 B2   11/2013 Ding
(Continued)

FOREIGN PATENT DOCUMENTS

EP    3 560 993 A1    10/2019
JP    H05-269196 A    10/1993
(Continued)

OTHER PUBLICATIONS

Nov. 19, 2021 Extended European Search Report issued in Patent Application No. 19881987.2.
(Continued)

*Primary Examiner* — Eli D. Strah
*Assistant Examiner* — Thomas J Kessler
(74) *Attorney, Agent, or Firm* — Oliff PLC (57) ABSTRACT

An artificial blood vessel that gives a sensation of needle insertion upon puncturing and a needle thread passability resembling those of blood vessels of animals including humans, and that has high liquid leakage preventability includes two or more layers which contain a component (A) hydrogenated block copolymer and a component (B) oil, at least one of the layers further containing a component (C) lubricant. It is preferable that the artificial blood vessel has a first peak load value of 0.01 N or more and 1.2 N or less upon needle penetration by puncturing at a speed of 1000 mm/min. under the condition of 23° C.±1° C. using a universal testing machine.

10 Claims, 1 Drawing Sheet (51) Int. Cl.
    *A61L 27/34*       (2006.01)
    *A61L 27/48*       (2006.01)
    *B32B 1/08*        (2006.01)
    *C08L 53/00*       (2006.01)

(52) U.S. Cl.
    CPC .............. *B32B 1/08* (2013.01); *C08L 53/005* (2013.01); *C08L 2203/02* (2013.01); *C08L 2205/06* (2013.01); *C08L 2207/322* (2013.01)

(58) Field of Classification Search
    CPC ...... C08L 53/005; C08L 53/025; C08L 91/00; C08L 2203/02; C08L 2205/06; C08L 2207/322; G09B 23/30
    See application file for complete search history.

(56) References Cited

U.S. PATENT DOCUMENTS

| | | | |
|---|---|---|---|
| 8,592,513 | B2 | 11/2013 | Fujiwara et al. |
| 9,102,849 | B2 | 8/2015 | Minamide et al. |
| 10,041,191 | B1 | 8/2018 | Tarutani |
| 10,487,249 | B2 | 11/2019 | Araki et al. |
| 10,781,305 | B2 | 9/2020 | Matsumoto et al. |
| 10,836,897 | B2 | 11/2020 | Miyama et al. |
| 11,124,593 | B2 | 9/2021 | Sukegawa et al. |
| 11,472,955 | B2 | 10/2022 | Sasaki et al. |
| 2009/0192250 | A1 | 7/2009 | Ijichi et al. |
| 2010/0056715 | A1 | 3/2010 | Wang |
| 2011/0245405 | A1 | 10/2011 | Jogo et al. |
| 2011/0319837 | A1 | 12/2011 | Jehara et al. |
| 2012/0190786 | A1 | 7/2012 | Sasaki |
| 2014/0102930 | A1 | 4/2014 | Sasaki |
| 2017/0044371 | A1 | 2/2017 | Ono |
| 2018/0030195 | A1* | 2/2018 | Oshita ..................... B32B 27/32 |
| 2018/0061279 | A1* | 3/2018 | Niimi ................... G09B 23/285 |
| 2018/0371250 | A1 | 12/2018 | Karube |
| 2019/0390054 | A1* | 12/2019 | Ishii ........................ C08L 91/00 |
| 2020/0022799 | A1* | 1/2020 | Yamashita ........... D03D 13/004 |
| 2020/0157339 | A1 | 5/2020 | Sasaki et al. |
| 2020/0362170 | A1 | 11/2020 | Karube |
| 2021/0330865 | A1 | 10/2021 | Miyama et al. |
| 2021/0340378 | A1 | 11/2021 | Miyama et al. |

FOREIGN PATENT DOCUMENTS

| | | |
|---|---|---|
| JP | H08-208964 A | 8/1996 |
| JP | H08-332218 A | 12/1996 |
| JP | H09-208836 A | 8/1997 |
| JP | 2001-181472 A | 7/2001 |
| JP | 2004-323552 A | 11/2004 |
| JP | 2014-186281 A | 10/2014 |
| JP | 2016-158765 A | 9/2016 |
| WO | 2008/072517 A1 | 6/2008 |
| WO | 2010/104068 A1 | 9/2010 |
| WO | 2015/162976 A1 | 10/2015 |
| WO | 2015/177926 A1 | 11/2015 |
| WO | 2017/042604 A1 | 3/2017 |
| WO | 2017/150714 A1 | 9/2017 |
| WO | 2018/097311 A1 | 5/2018 |
| WO | 2018/117212 A1 | 6/2018 |
| WO | 2018/151320 A1 | 8/2018 |

OTHER PUBLICATIONS

Dec. 24, 2019 Search Report issued in International Patent Application No. PCT/JP2019/041851.

\* cited by examiner

ARTIFICIAL BLOOD VESSEL

TECHNICAL FIELD

The present invention relates to artificial blood vessels.

BACKGROUND ART

Artificial blood vessels, other than in vivo grafting, are used in various fields such as medical simulators for acquiring puncturing skills in surgical treatment, etc. Patent Document 1 proposes an artificial blood vessel containing, as a fiber-reinforced resin, a block copolymer, etc. formed from a polymeric block having styrene as a main component and a polymeric block having a conjugated diene compound as a main component. This technology is believed to enable the provision of an artificial blood vessel of high strength. Patent Document 2 proposes a resin composition containing prescribed amounts of a hydrogenated block copolymer having a prescribed MFR, an oil, and a polyolefin-based resin having a prescribed specific surface area. This technology enables the achievement of a softer resin composition in which high loading of oil is possible and bleed-outs can be suppressed.

CITATION LIST

Patent Literature

Patent Document 1: JP 2014-186281 A
Patent Document 2: WO 2018/151320 A

SUMMARY OF INVENTION

Technical Problem

Artificial blood vessels are required to resemble blood vessels of animals including humans, in terms of the sensation of insertion upon puncturing and passability for needles and threads (hereinafter also referred to as "needle thread passability"). Moreover, in cases where artificial blood vessels are used as medical simulators for acquiring puncturing skills, the amount of liquid leakage will increase after several times of puncturing in the process of repeated puncturing practice, resulting in a need to stop practicing and exchange the artificial blood vessel. Thus, artificial blood vessels need to have high liquid leakage preventability so as to decrease the frequency of exchanges during practice.

The present invention addresses the problem of providing artificial blood vessels that provide a sensation of needle insertion upon puncturing and a needle thread passability resembling those of blood vessels of animals including humans, and that have high liquid leakage preventability.

Solution to Problem

In the process of their research, the present inventors learned that when the sensation of needle insertion upon puncturing and the needle thread passability are made to approach those of blood vessels of animals including humans, liquid leakage preventability decreases, and contrarily, when liquid leakage preventability is increased, the sensation of needle insertion and the needle thread passability decrease. The present inventors conducted further research and discovered that by configuring so as to have a plurality of layers containing a hydrogenated block copolymer and an oil, in which at least one of the layers further contains a lubricant, a sensation of needle insertion and a needle thread passability can be achieved together with high liquid leakage preventability, which is at a trade-off therewith, arriving at the completion of the present invention.

The present invention relates to the following.

[1] An artificial blood vessel having two or more layers which contain a component (A) hydrogenated block copolymer and a component (B) oil, at least one of the layers further containing a component (C) lubricant.

[2] The artificial blood vessel according to [1], wherein the artificial blood vessel is tubular.

[3] The artificial blood vessel according to [1] or [2], wherein the artificial blood vessel has a first peak load value of 0.01 N or more and 1.2 N or less upon needle penetration by puncturing at a speed of 1000 mm/min. under a condition of 23° C.±1° C. using a universal testing machine.

[4] The artificial blood vessel according to any one of [1] to [3], wherein the artificial blood vessel has a load value of 0.1 N or more and 1 N or less applied on a puncture needle and/or a load value of 0.01 N or more and 0.1 N or less applied on a medical thread, when punctured at a speed of 1000 mm/min. using a universal testing machine provided with a puncture needle and a medical thread.

[5] The artificial blood vessel according to any one of [1] to [4], wherein the artificial blood vessel, after puncturing 50 times with an injection needle, has a liquid leakage amount of 10 mL or less in 60 sec. under a pressure of 60 mmHg.

[6] The artificial blood vessel according to any one of [1] to [5], wherein the artificial blood vessel has one or more layers formed using a resin composition I containing: 100 parts by mass of the component (A) hydrogenated block copolymer; 300 parts by mass or more and 1000 parts by mass or less of the component (B) oil; and 0.1 parts by mass or more and 150 parts by mass or less of the component (C) lubricant.

[7] The artificial blood vessel according to any one of [1] to [6], wherein the artificial blood vessel has, on an interior of the layer formed using the resin composition I, a layer formed using a resin composition II that has a different constitution from the resin composition I, the resin composition II containing: 100 parts by mass of the component (A) hydrogenated block copolymer; 50 parts by mass or more and 1000 parts by mass or less of the component (B) oil; and less than 0.1 parts by mass of the component (C) lubricant.

[8] The artificial blood vessel according to any one of [1] to [7], wherein the artificial blood vessel has, on an exterior of the layer formed using the resin composition I, a layer formed using a resin composition III that has a different constitution from the resin composition I, the resin composition III containing: 100 parts by mass of the component (A) hydrogenated block copolymer; 50 parts by mass or more and 1000 parts by mass or less of the component (B) oil; and less than 0.1 parts by mass of the component (C) lubricant.

[9] The artificial blood vessel according to any one of [1] to [8], wherein the component (C) lubricant contains at least one lubricant selected from the group consisting of an ionic surfactant and a nonionic surfactant.

[10] The artificial blood vessel according to any one of [1] to [9], wherein the component (A) hydrogenated block copolymer has a MFR (temperature 230° C., load 2.16 kg) of 1 g/10 min. or less.

[11] The artificial blood vessel according to any one of [1] to [10], wherein the component (B) oil has a kinematic viscosity of 0.1-100 $mm^2/s$ at 37.8° C. or 40° C.

Effects of Invention

According to the present invention, it is possible to provide artificial blood vessels that provide a sensation of needle insertion upon puncturing and a needle thread passability resembling those of blood vessels of animals including humans, and that have high liquid leakage preventability.

DESCRIPTION OF EMBODIMENTS

An embodiment of the present invention shall be explained in detail below. The present invention is not limited to the following embodiment and can be carried out with modifications as appropriate so long as the effects of the invention are not inhibited. Further, in the present invention, "A-B" means A or more and B or less.
Artificial Blood Vessel An artificial blood vessel according to the present embodiment has two or more layers containing a component (A) hydrogenated block copolymer and a component (B) oil, in which at least one of the layers further contains a component (C) lubricant. This allows the achievement of a sensation of needle insertion upon puncturing and a needle thread passability that resemble those of blood vessels of animals including humans, together with high liquid leakage preventability.
(Sensation of Needle Piercing and Insertion)

The artificial blood vessel preferably has a first peak load value of 0.01 N or more and 1.2 N or less, more preferably 0.01 N or more and 1 N or less, and even more preferably 0.01 N or more and 0.5 N or less, upon needle penetration by puncturing at a speed of 1000 mm/min. under the condition of 23° C.±1° C. using a universal testing machine. This enables the making of an artificial blood vessel that provides a sensation of needle piercing and insertion (response) resembling that of blood vessels of animals including humans when punctured. As a result thereof, the artificial blood vessel can be preferably used in, e.g., a medical simulator for injection practice. Moreover, the artificial blood vessel preferably has a displacement of 1 mm or more and 50 mm or less and more preferably 1 mm or more and 20 mm or less, upon needle penetration by puncturing at a speed of 1000 mm/min. under the condition of 23° C.±1° C. using a universal testing machine.

The sensation of needle piercing and insertion, specifically, can be evaluated by measuring the first peak load value (N) and/or displacement (mm) upon needle penetration when punctured at a speed of 1000 mm/min. under the condition of 23° C.±1° C. using a universal testing machine (e.g., Autograph AG-Xplus testing machine manufactured by Shimadzu Corporation) on a test piece (thickness 2-3 mm, length 360 mm×inner diameter 6-7 mm, outer diameter 11-12 mm). The size of the needle is determined on the basis of whether the needle is for injection practice or for suturing practice, but can, for example, be an injection needle having an outer diameter of 0.1-2.7 mm and a needle gauge size of ultrafine 0.1-12 G.

The sensation of needle piercing and insertion can be adjusted by, e.g., changing the formulation of the materials constituting each layer, the thickness of each layer, and/or the overall thickness. For example, liquid leakage preventability can be increased by, e.g., adjusting the contents of the component (A) hydrogenated block copolymer and the component (B) oil in the outermost layer or by adjusting the thickness of the outermost layer.

(Needle Thread Passability)

The artificial blood vessel preferably has a load value (needle passability) of 0.1 N or more and 1 N or less and more preferably 0.1 N and 0.5 N or less, applied on a puncture needle, when punctured at a speed of 1000 mm/min. using a universal testing machine provided with a puncture needle and a medical thread.

The artificial blood vessel preferably has a load value (thread passability) of 0.01 N or more and 0.1 N or less and more preferably 0.01 N and 0.05 N or less, applied on a medical thread, when punctured at a speed of 1000 mm/min. using a universal testing machine provided with a puncture needle and a medical thread. This enables the realization of a needle thread passability resembling that of human blood vessels when punctured and/or sutured. As a result thereof, the artificial blood vessel can be preferably used in, e.g., a medical simulator for puncturing and/or suturing practice.

With respect to methods for measuring needle piercing resistance values and thread passing resistance values, specifically, an oblong test piece is punctured at a speed of 1000 mm/min. using Autograph AG-Xplus testing machine manufactured by Shimadzu Corporation, and load values (N) applied on the puncture needle and medical thread are measured. The thickness and the size of the test piece are determined on the basis of the site of interest simulated by the medical simulator, but for example, can be oblong test pieces of 30 mm×25 mm×thickness 2-3 mm. The oblong test piece can be made by, for example, cutting open an artificial blood vessel. The size of the needle is determined on the basis of whether the needle is for injection practice or for suturing practice, but for example, a needle the same as that described above can be used. The size of the thread is determined on the basis of the site of interest simulated by the medical simulator, but for example, those with the size of medical silk suture threads or nonabsorbable plastic suture threads, or size number 12-0 to number 10 can be used.

The needle piercing resistance values and thread passing resistance values can be adjusted by, e.g., changing the formulation of the materials constituting each layer, the thickness of each layer, and/or the overall thickness. For example, needle piercing resistance values and thread passing resistance values can be adjusted by adjusting the content of the component (C) lubricant in the intermediate layer, the thickness of the intermediate layer, etc.
(Liquid Leakage Preventability)

The artificial blood vessel, after being punctured 50 times with an injection needle, preferably has a liquid leakage amount of 10 mL or less and more preferably 5 mL or less in 60 sec. under a pressure of 60 mmHg. This enables the achievement of an artificial blood vessel having a liquid leakage preventability (a property that prevents blood from leaking) close to that of blood vessels of animals including humans when punctured.

Liquid leakage preventability can be evaluated, specifically, by puncturing a tubular test piece (thickness: 2 mm, length: 360 mm, inner diameter: 4 mm) 50 times with an injection needle at a non-penetrating angle (20°-30°) up to a depth of 30 mm, then applying a pressure of 60 mmHg, and measuring the amount of liquid leaked in 60 sec. with an electronic balance. The size of the injection needle can be determined on the basis of the site of interest simulated by the medical simulator on which puncturing is performed, but for example, the injection needles can have an outer diameter of 0.1-2.7 mm and a needle gauge size of ultrafine 0.1-12 G.

The liquid leakage preventability can be adjusted by, e.g., changing the formulation of the materials constituting each layer, the thickness of each layer, and/or the overall thickness. For example, liquid leakage preventability can be increased by, e.g., adjusting the contents of the component (A) hydrogenated block copolymer and the component (B) oil in the innermost layer or by adjusting the thickness of the innermost layer, etc.

(Resin Composition I)

The artificial blood vessel has one or more layers formed using a resin composition I containing a component (A) hydrogenated block copolymer, a component (B) oil, and a component (C) lubricant at prescribed amounts. The resin composition I, in addition to the component (A) hydrogenated block copolymer and the component (B) oil, further contains the component (C) lubricant, and can thus provide a molded article having a sensation of needle insertion and a needle thread passability that resemble those of animals including humans.

<Component (A) Hydrogenated Block Copolymer>

The component (A) hydrogenated block copolymer preferably contains one or more hydrogenated products (hydrogen-added products or hydrides) of an aromatic vinyl-conjugated diene block copolymer containing a block unit (X) derived from an aromatic vinyl compound and a block unit (Y) derived from a conjugated diene.

Forms of aromatic vinyl-conjugated diene block copolymers having such a configuration are represented by, for example, $X(YX)_n$ or $(XY)_n$ (where n is an integer of 1 or greater). Among these, those with the form $X(YX)_n$, particularly those with the form X—Y—X, are preferred. The X—Y—X form is preferably at least one copolymer selected from the group consisting of a polystyrene-polybutadiene-polystyrene block copolymer, a polystyrene-polyisoprene-polystyrene block copolymer, and a polystyrene-polyisoprene/butadiene-poly styrene block copolymer.

In such an aromatic vinyl-conjugated diene block copolymer, the aromatic vinyl block unit (X), which is a hard segment, exists as a cross-linking point for the conjugated diene rubber block unit (Y) and forms a pseudo cross-link (domain). This conjugated diene rubber block unit (Y) that is present between the aromatic vinyl block units (X) is a soft segment and exhibits rubber elasticity.

Examples of aromatic vinyl compounds that form the block unit (X) include styrene, α-methylstyrene, 3-methylstyrene, p-methylstyrene, 4-propyl styrene, 4-dodecylstyrene, 4-cyclohexylstyrene, 2-ethyl-4-benzylstyrene, 4-(phenylbutyl)styrene, 1-vinylnaphthalene, and 2-vinylnaphthalene, etc. Among these, styrene is preferred.

Examples of conjugated dienes that form the block unit (Y) include butadiene, isoprene, pentadiene, 2, 3-dimethyl butadiene, and combinations thereof, etc. Among these, at least one conjugated diene selected from the group consisting of butadiene, isoprene, and a combination of butadiene and isoprene (copolymer unit of butadiene-isoprene) is preferred. It is also possible to use one or more of these conjugated dienes in combination. The conjugated diene block unit (Y) formed from butadiene-isoprene copolymer units may be any of a random copolymer unit of butadiene and isoprene, a block copolymer unit thereof, or a tapered copolymer unit thereof.

In an aromatic vinyl-conjugated diene block copolymer as described above, the content of the aromatic vinyl block unit (X) is preferably 5 mass % or more and 50 mass % or less, and more preferably 20 mass % or more and 40 mass % or less. The content of this aromatic vinyl unit can be measured by a normal method such as infrared spectroscopy, NMR spectroscopy, etc.

Aromatic vinyl-conjugated diene block copolymers such as those described above can be produced by various methods. Examples of production methods include (1) a method of consecutively polymerizing an aromatic vinyl compound and then a conjugated diene using an alkyl lithium compound such as n-butyllithium as an initiator, (2) a method of polymerizing an aromatic vinyl compound and then a conjugated diene, and coupling the same by means of a coupling agent, and (3) a method of consecutively polymerizing a conjugated diene and then an aromatic vinyl compound using a lithium compound as an initiator.

The hydrogenated block copolymer is a product (hydrogen-added product or hydride) of an aromatic vinyl-conjugated diene block copolymer such as those described above hydrogenated by a publicly known method, wherein the preferred hydrogenation rate is 90 mol % or more. This hydrogenation rate is a value when the entire amount of carbon-carbon double bonds in the conjugated diene block unit (Y) is set as 100 mol %. A "hydrogenation rate of 90 mol % or more" indicates that 90 mol % or more of the carbon-carbon double bonds are hydrogenated. Examples of such hydrogenated block copolymers include polystyrene-poly(ethylene/propylene) block (SEP), polystyrene-poly(ethylene/propylene) block-polystyrene (SEPS), polystyrene-poly(ethylene/butylene) block-polystyrene (SEBS), polystyrene-poly(ethylene-ethylene/propylene) block-polystyrene (SEEPS), etc. More specific examples include SEPTON (manufactured by Kuraray Co. Ltd.), Kraton (manufactured by Shell Chemicals), Kraton G (manufactured by Shell Chemicals), and Tuftec (manufactured by Asahi Kasei Corp.) (the above are proprietary names). They may be used individually or in combination. Among them, it is preferable that SEEPS is included as the component (A).

The melt flow rate (MFR (temperature 230° C., load 2.16 kg)) of the component (A) hydrogenated block copolymer is 1 g/10 min. or less and is preferably less than 0.1 g/10 min. "MFR (temperature 230° C., load 2.16 kg)" refers to MFR measured under the conditions of a temperature of 230° C. and a load of 2.16 kg in accordance with JIS K7210. By making MFR within the above range, bleed-out (oil seepage) occurrences can be prevented when oil is added, and reductions in mechanical strength can also be prevented. The hydrogenation rate is measured by a publicly known method such as nuclear magnetic resonance (NMR) spectroscopy.

In terms of oil absorption work before kneading, it is preferable that the form of the component (A) hydrogenated block copolymer is a powder or an amorphous (crumb) form.

<Component (B) Oil>

As the component (B) oil, most preferred examples include mineral oil-based oils such as paraffin-based process oil, naphthene-based process oil, aromatic-based process oil, and liquid paraffin, and silicon oil, castor oil, linseed oil, olefin-based wax, mineral-based wax, etc. Among these, paraffin-based and/or naphthene-based process oils are preferred. Examples of the process oil include the Diana Process Oil series (manufactured by Idemitsu Kosan Co., Ltd.), JOMO Process P (manufactured by Japan Energy Corporation), etc. Moreover, it is also possible to use various ester-based plasticizers that are phthalic acid-based, trimellitic acid-based, pyromellitic acid-based, adipic acid-based, or citric acid-based. They may be used individually or in combination.

In terms of workability, it is preferable that the component (B) oil is pre-absorbed in advance in the component (A) hydrogenated block copolymer. To do so, it is preferable that the form of the component (A) hydrogenated block copolymer is a powder or an amorphous (crumb) form, which absorbs oil easily.

The component (B) oil preferably has a kinematic viscosity at 37.8° C. or 40° C. of 0.1-100 mm$^2$/s, more preferably 0.1-50 mm$^2$/s, and even more preferably 0.1-15 mm$^2$/s. By making the kinematic viscosity within the above range, a resin composition that leads to a biological model, which has a softness and physical properties resembling those of human blood vessels and/or skin, can be obtained. Kinematic viscosity measurements can be made by measuring at a test temperature of 37.8° C. or 40° C. using a Cannon-Fenske viscometer according to JIS K 2283:2000 "5. Kinematic Viscosity Testing Method."

<Component (C) Lubricant>

As the component (C) lubricant, examples include ionic surfactants, nonionic surfactants, hydrocarbon-based glidants, fatty acid-based glidants, aliphatic amide-based glidants, metallic soap-based glidants, ester-based glidants, etc.

As the ionic surfactant, an anionic surfactant, a cationic surfactant, or an amphoteric surfactant can be used. Examples of the anionic surfactant include fatty acids sodium, monoalkyl sulfates, alkylpolyoxyethylene sulfates, alkylbenzene sulfonates, monoalkyl phosphates, etc. Examples of commercial products include the proprietary name "Electrostripper PC" manufactured by Kao Corporation, etc.

Examples of cationic surfactants include alkyltrimethylammonium salts, dialkyldimethylammonium salts, alkylbenzyldimethylammonium salts, etc.

Examples of amphoteric surfactants include alkyldimethylamine oxides, alkylcarboxybetaines, etc.

Examples of nonionic surfactants include polyoxyethylene alkyl ethers, fatty acid sorbitan esters, alkylpolyglucosides, fatty acid diethanolamides, alkylmonoglyceryl ethers, etc. Examples of commercial products include the proprietary name "Electrostripper EA" manufactured by Kao Corporation, etc.

Examples of hydrocarbon-based glidants include paraffin wax, synthetic polyethylene wax, octyl alcohol, etc. Examples of fatty acid-based glidants include stearic acid, stearyl alcohol, etc.

Examples of aliphatic amide-based glidants include fatty acid amides such as stearamide, oleamide, and erucamide; alkylene fatty acid amides such as methylene bis stearamide, ethylene bis stearamide; etc. Examples of metallic soap-based glidants include metal stearates, etc.

Examples of ester-based glidants include fatty acid esters of alcohols, monoglyceride stearate, stearyl stearate, hydrogenated oils, etc.

For the component (C) lubricant, one or more selected from the above lubricants can be used. Among them, in terms of having a softness and physical properties better resembling those of human blood vessels and/or skin, it is preferable that one or more lubricants selected from the group consisting of ionic surfactants and nonionic surfactants are included, and it is more preferable that one or more selected from nonionic surfactants are included.

(Content)

The resin composition I preferably has a constitution containing: 100 parts by mass of the component (A) hydrogenated block copolymer; 300 parts by mass or more and 1000 parts by mass or less, and more preferably 300 parts by mass or more and 600 parts by mass or less, of the component (B) oil; and 0.1 parts by mass or more and 150 parts by mass or less, more preferably 0.1 parts by mass or more and 100 parts by mass or less, and even more preferably 0.1 parts by mass or more and 50 parts by mass or less, of the component (C) lubricant. By using the above constitution, a sensation of needle piercing and insertion and a needle thread passability resembling those of human blood vessels can be more easily realized.

Additives, Etc.

The resin composition I may contain, as necessary, rubber, a plasticizer, a filler or stabilizer, an antioxidant, a light resistance improver, an ultraviolet absorber, a softener, a glidant, a processing aid, a colorant, an anti-static agent, an anti-fogging agent, an anti-blocking agent, a crystal nucleating agent, a foaming agent, etc.

The resin composition I may contain, as necessary, another resin or elastomer. There are no particular restrictions with respect to this other resin or elastomer, but examples thereof include polyolefins such as polyethylene, polypropylene, ethylene-propylene copolymer, and ethylene-vinyl acetate copolymer (EVA); styrene-based thermoplastic elastomers such as styrene-butadiene copolymer, styrene-isoprene copolymer, styrene-butadiene-isoprene copolymer, styrene-ethylene-butadiene-styrene copolymer (SEBS), and styrene-ethylene-propylene-styrene copolymer (SEPS); acrylonitrile-butadiene-styrene copolymer (ABS resin), acrylonitrile-styrene copolymer (AS resin), polystyrene, polyvinyl chloride, polyvinylidene chloride, fibrous fillers, etc. When the other resin or elastomer is included, the content thereof is preferably 0.01 parts by mass or more and 500 parts by mass or less in the resin composition.

In terms of production costs and balance of physical properties, the resin composition I is preferably thermoplastic.

(Production Method)

The method for producing the resin composition I is not limited in particular, and a publicly known, appropriate blending method can be used. For example, melt-kneading can be performed with a single screw extruder, a twin-screw extruder, a Banbury type mixer, a plastomill, a co-kneader, a heating roll, etc. Before melt-kneading is performed, the raw materials may be mixed uniformly by a Henschel mixer, a ribbon blender, a super mixer, a tumbler, etc. The melt-kneading temperature is not limited in particular, but is generally 50-300° C., and preferably 70-250° C.

(Layer Configuration)

The artificial blood vessel may have two or more layers formed using the above-mentioned resin composition I. In terms of being able to easily achieve a sensation of needle piercing and insertion and a needle thread passability together with liquid leakage preventability, the artificial blood vessel preferably has, on an exterior of a first layer formed using the resin composition I, a second layer formed using a resin composition II having a different constitution from the resin composition I. Further, it is preferable that the artificial blood vessel has, on an interior of the first layer formed using the resin composition I, a third layer formed using a resin composition III having a different constitution from the resin composition I. Here, a "different constitution" means that the types of compounds and/or contents thereof constituting the component (A) hydrogenated block copolymer, the component (B) oil, and the component (C) lubricant that may be included as necessary, as well as additives that may be included as necessary, are different.

(Resin Composition II)

The resin composition II contains a component (A) hydrogenated block copolymer and a component (B) oil, and can contain a component (C) lubricant, as necessary. The resin composition II has a different constitution from the resin composition I and preferably contains 100 parts by mass of the component (A) hydrogenated block copolymer and 50 parts by mass or more and 1000 parts by mass or less, more preferably 150 parts by mass or more and 500 parts by mass or less, of the component (B) oil. The content of the component (C) lubricant is less than 0.1 parts by mass and preferably less than 0.05 parts by mass. The resin composition II may be free of the component (C) lubricant.

By having a second layer formed using the resin composition II having such a constitution, as a layer on the exterior (e.g., the outermost layer of the artificial blood vessel) of the first layer, a sensation of needle piercing and insertion resembling that of animals including humans can be more easily realized.

The component (A) hydrogenated block copolymer, the component (B) oil, and the component (C) lubricant that may be included as necessary, as well as an additive that may be included as necessary in the resin composition II can be selected from those given as examples for the above-mentioned resin composition I. The physical properties, shapes, etc. of the component (A) hydrogenated block copolymer, the component (B) oil, and the component (C) lubricant that may be included as necessary can also be the same as those for the above-mentioned resin composition I. Moreover, the method for producing the resin composition II can also be the same method performed for the above-mentioned resin composition I.

(Resin Composition III)

The resin composition III contains a component (A) hydrogenated block copolymer and a component (B) oil, and can contain a component (C) lubricant, as necessary. The resin composition III has a different constitution from the resin composition I and preferably contains 100 parts by mass of the component (A) hydrogenated block copolymer and 50 parts by mass or more and 1000 parts by mass or less, more preferably 150 parts by mass or more and 500 parts by mass or less, of the component (B) oil. The content of the component (C) lubricant is less than 0.1 parts by mass and preferably less than 0.05 parts by mass. The resin composition III may be free of the component (C) lubricant.

By having a third layer formed using the resin composition III having such a constitution, as a layer on the interior (e.g., the innermost layer of the artificial blood vessel) of the first layer, high liquid leakage preventability can be easily realized while maintaining a sensation of needle piercing and insertion and a needle thread passability resembling those of human blood vessels.

The constitutions of the resin composition II and the resin composition III may be the same or different, but in terms of workability, it is preferable that the resin composition II and the resin composition III have the same constitution.

The component (A) hydrogenated block copolymer, the component (B) oil, and the component (C) lubricant that may be included as necessary, as well as an additive that may be included as necessary in the resin composition III can be selected from those given as examples for the above-mentioned resin composition I. The physical properties, shapes, etc. of the component (A) hydrogenated block copolymer, the component (B) oil, and the component (C) that may be included as necessary can also be the same as those for the above-mentioned resin composition I. Moreover, the method for producing the resin composition III can also be the same method performed for the above-mentioned resin composition I.

The number of layers of the artificial blood vessel is two or more, can be two or more and five or less, and e.g., can be composed of three layers. In the case of a three-layer configuration, it is possible to configure so as to have, on an exterior of a first layer formed using the resin composition I, a second layer formed using the resin composition II, and so as to further have, on an interior of the first layer formed using the resin composition I, a third layer formed using the resin composition III. In this case, the resin composition II and the resin composition III can have the same constitution. That is, the second layer and the third layer can be composed of the resin composition II (or the resin composition III). With this configuration, in the case of an artificial blood vessel of a three-layer structure, a sensation of needle piercing and insertion and a needle thread passability resembling those of blood vessels, together with high liquid leakage preventability, can be more easily achieved.

Figure 1:
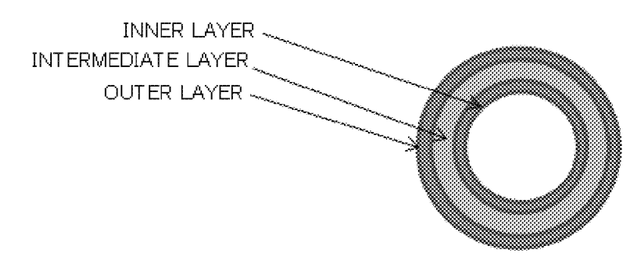
FIG. 1 is a cross-sectional view showing a configuration example of an artificial blood vessel.

FIG. 1 shows a cross-sectional view of one configuration example of an artificial blood vessel composed of three layers. The artificial blood vessel shown in FIG. 1 is composed of three layers, overlaid from the interior in the order of an inner layer, an intermediate layer, and an outer layer. In the example of FIG. 1, the inner layer, the intermediate layer, and the outer layer may be formed with a first layer formed using the resin composition I, but in terms of being able to easily achieve a sensation of needle piercing and insertion and a needle thread passability better resembling those of human blood vessels, together with high liquid leakage preventability, it is preferable that the intermediate layer is formed from a first layer formed using the resin composition I, and the outer layer and the inner layer are each formed from a second layer formed using the resin composition II or a third layer formed using the resin composition III. For example, the inner layer and the outer layer can be each composed of a layer formed using the resin composition II, and the intermediate layer can be composed of a layer formed using the resin composition I (containing a component (C) lubricant).

The layers constituting the artificial blood vessel can each have the same thickness as the blood vessel of interest. For example, the first layer (e.g., the intermediate layer in FIG. 1) formed using the resin composition I can have a thickness of 0.5 mm to 1.5 mm, the second layer (e.g., the outer layer in FIG. 1) formed using the resin composition II can have a thickness of 0.1 mm to 1 mm, and the third layer (e.g., the inner layer in FIG. 1) formed using the resin composition III can have a thickness of 0.4 mm to 1.5 mm. By setting these ranges, a sensation of needle piercing and insertion and a needle thread passability resembling those of human blood vessels, together with liquid leakage preventability, can be easily achieved.

The shape of the artificial blood vessel is preferably tubular. The method for producing the artificial blood vessel is not limited in particular, and the artificial blood vessel can be produced by a publicly known molding method. For example, various molding methods such as extrusion molding, cast molding, injection molding, vacuum molding, blow molding, etc. may be used to match the target organ model.

An artificial blood vessel according to the present embodiment provides a sensation of needle insertion upon puncturing and a passability for needles and threads resembling those of blood vessels of animals including humans, as well as high liquid leakage preventability, and thus can be preferably used as a member for a medical simulator.

EXAMPLES

The present invention shall be explained in more detail by referring to the examples below, but interpretation of the present invention is not to be limited by these examples.

Materials used in the production of the resin compositions are shown below. In addition, the MFR values below are values obtained at a temperature of 230° C. and a load of 2.16 kg.

[Materials]

<Component (A) Hydrogenated Block Copolymer>
  A-1: SEEPS, "SEPTON4033" manufactured by Kuraray Co. Ltd., MFR 1 g/10 min., styrene content 30 mass %
  A-2: SEEPS, "SEPTON-4055" manufactured by Kuraray Co. Ltd., MFR 1 g/10 min., styrene content 30 mass %
  A-3: SEEPS, "SEPTON-J" manufactured by Kuraray Co. Ltd., MFR 1 g/10 min., styrene content 40 mass %

<Component (B) Oil>
  B-1: Paraffin-based oil, "PW-90" manufactured by Idemitsu Kosan, Co., Ltd., kinematic viscosity 90.5 $mm^2/s$ at 40° C.
  B-2: Paraffin-based oil, "PARLEAM EX" manufactured by NOF Corporation, kinematic viscosity 10.6 $mm^2/s$ at 37.8° C.

<Component (C) Lubricant>
  C-1: "Electrostripper EA" manufactured by Kao Corporation

[Resin Composition Production Example 1: Formulation 1]

A Brabender Plasti-Corder (PL2000 manufactured by Brabender GmbH) was used to knead 100 parts by mass of a hydrogenated block copolymer (A-1) and 300 parts by mass of an oil (B-1) for six minutes at 150° C. and a rotation speed of 50 revolutions/min. to obtain a resin composition. The hydrogenated block copolymer (A-1) was supplied from the maker as an amorphous powder. Several days before kneading, a prescribed amount of the oil (B-1) was dripped onto the hydrogenated block copolymer (A-1) and allowed to sufficiently infiltrate. Here, the amount of the oil (B-1) allowed to infiltrate is included in the above blending quantities.

[Resin Composition Production Example 2: Formulation 2]

Other than using 200 parts by mass of the oil (B-1) to 100 parts by mass of the hydrogenated block copolymer (A-1), a resin composition was obtained in the same manner as in Production Example 1.

[Resin Composition Production Example 3: Formulation 3]

A Brabender Plasti-Corder (PL2000 manufactured by Brabender GmbH) was used to knead 100 parts by mass of a hydrogenated block copolymer (A-2), 500 parts by mass of an oil (B-2), and 36 parts by mass of a glidant (C-1) for six minutes at 150° C. and a rotation speed of 50 revolutions/min. to obtain a resin composition. The hydrogenated block copolymer (A-2) was supplied from the maker as an amorphous powder. Several days before kneading, the glidant (C-1) was dripped onto the hydrogenated block copolymer (A-2) and allowed to sufficiently infiltrate, and then the oil (B-2) was dripped and allowed to infiltrate. Here, the amounts of the oil (B-2) and the glidant (C-1), which were allowed to infiltrate, are included in the above blending quantities.

[Resin Composition Production Example 4: Formulation 4]

Other than using a hydrogenated block copolymer (A-3) instead of the hydrogenated block copolymer (A-2), a resin composition was obtained in the same manner as in Production Example 3.

Example 1

An extruder provided with a three-layer head was used to make an artificial blood vessel having an outer diameter of 11.54 mm, an inner diameter of 6.90 mm, and a thickness of 2.32 mm, and configured to have an inner layer (thickness 0.79 mm) and an outer layer (0.66 mm) composed of the resin composition obtained in Production Example 2 (Formulation 2) and an intermediate layer (thickness 0.88 mm) composed of the resin composition obtained in Production Example 3 (Formulation 3). The outer diameter, inner diameter, and thickness were measured using an opto-digital microscope DSX500 manufactured by OLYMPUS Corporation.

Examples 2 to 10 and Comparative Examples 1 to 8

Other than using the resin compositions shown in Table 1 and the configurations, dimensions, etc. shown in Table 2, artificial blood vessels were made in the same manner as Example 1. Comparative Examples 1 to 3 are examples of cases in which three layers or a single layer was molded using a resin composition free of lubricant, Comparative Examples 4 and 5 are examples of cases in which a single layer was molded using a resin composition containing a lubricant, Comparative Example 6 and 7 are examples of cases in which a single layer was molded using silicone or polyurethane, and Comparative Example 8 is an example of a case in which three layers were molded using natural rubber.

[Measurement and Evaluation]

Physical properties were measured and evaluated as follows for the artificial blood vessels obtained in the examples and comparative examples. Moreover, as Reference Examples 1 to 3, porcine aorta, vena cava, and carotid samples (20 mm×20 mm, thickness as shown in Table 1) were prepared.

(Sensation of Needle Piercing and Insertion)

The artificial blood vessels of the examples and comparative examples were cut open to make oblong test pieces. The sensation of needle piercing and insertion was evaluated by measuring the first peak load value (intensity) and the displacement upon needle penetration when punctured at a speed of 1000 m/min under the condition of 23±1° C. with an Autograph AG-Xplus testing machine manufactured by Shimadzu Corporation. The sensation of needle piercing and insertion was evaluated on the basis of the criteria below.

4: First peak load value upon needle penetration is 0.1 N or more and 0.3 N or less.
  3: First peak load value upon needle penetration is greater than 0.3 N and 0.6 N or less.
  2: First peak load value upon needle penetration is greater than 0.6 N and 1.2 N or less.
  1: First peak load value upon needle penetration is greater than 1.2 N.

(Liquid Leakage Preventability)

A flow rate pump was used to circulate water at 80 mL/min inside the artificial blood vessels, the pressure was adjusted to 60 mmHg, and after puncturing 50 times with an injection needle (size: 17 G), the amount of liquid leakage in 60 sec. was measured with an electronic balance. Liquid leakage preventability was evaluated on the basis of the criteria below.

4: 1 mL or less
  3: Greater than 1 mL and 5 mL or less
  2: Greater than 5 mL and 10 mL or less
  1: Greater than 10 mL (Puncture Needle/Medical Thread Passability: Needle Thread Passability)

The artificial blood vessels of the examples and comparative examples were cut open to make oblong test pieces. Load values applied on puncture needles (size: 17 G) and medical threads (size: 4-0 made of polypropylene) were each measured using an Autograph AG-Xplus manufactured by Shimadzu Corporation at a speed of 1000 mm/min. Needle passability and thread passability were evaluated on the basis of the criteria below.

Needle Passability
    4: 0.1 N or more and less than 0.3 N
    3: 0.3 N or more and less than 0.6 N
    2: 0.6 N or more and 1 N or less
    1: Greater than 1 N Thread Passability
    4: 0.01 N or more and less than 0.03 N
    3: 0.03 N or more and less than 0.06 N
    2: 0.06 N or more and 0.1 N or less
    1: Greater than 0.1 N

TABLE 1

|  | Component (A) (parts by mass) | Component (B) (parts by mass) | Component (C) (parts by mass) |
|---|---|---|---|
| Formulation 1 | A-1 100 | B-1 300 | — |
| Formulation 2 | A-1 100 | B-1 200 | — |
| Formulation 3 | A-2 100 | B-2 500 | C-1 36 |
| Formulation 4 | A-3 100 | B-2 500 | C-1 36 |

TABLE 2

| | Layer Config. | | Inner Layer | Interm. Layer | Outer Layer | Dimensions Thickness (mm) | Outer Diameter (mm) | Inner Diameter (mm) | Thread Passability Resistance (N) | Thread Passability Eval | Needle Passability Resistance (N) | Needle Passability Eval | Sensation of Needle Piercing and Insertion Intensity (N) | Displacement (mm) | Eval | Liquid Leakage Preventability Leakage (mL) | Eval |
|---|---|---|---|---|---|---|---|---|---|---|---|---|---|---|---|---|---|
| Ex. 1 | 3 layers | Formulation Thickness (mm) | Form. 2 / 0.79 | Form. 3 / 0.88 | Form. 2 / 0.66 | 2.32 | 11.54 | 6.90 | 0.037 | 3 | 0.39 | 3 | 0.50 | 14.1 | 3 | 0.82 | 4 |
| Ex. 2 | 3 layers | Formulation Thickness (mm) | Form. 2 / 0.62 | Form. 3 / 0.94 | Form. 2 / 0.58 | 2.14 | 11.51 | 7.23 | 0.039 | 3 | 0.42 | 3 | 0.55 | 14.1 | 3 | 1.23 | 3 |
| Ex. 3 | 3 layers | Formulation Thickness (mm) | Form. 2 / 0.46 | Form. 3 / 1.00 | Form. 2 / 0.40 | 1.86 | 7.67 | 3.94 | 0.033 | 3 | 0.35 | 3 | 0.46 | 14.9 | 3 | 3.17 | 3 |
| Ex. 4 | 3 layers | Formulation Thickness (mm) | Form. 2 / 0.57 | Form. 3 / 1.28 | Form. 2 / 0.39 | 2.24 | 8.94 | 4.46 | 0.036 | 3 | 0.38 | 3 | 0.49 | 14.8 | 3 | 2.75 | 3 |
| Ex. 5 | 3 layers | Formulation Thickness (mm) | Form. 2 / 0.69 | Form. 3 / 0.80 | Form. 2 / 0.38 | 1.87 | 7.77 | 4.03 | 0.349 | 3 | 0.68 | 2 | 2.72 | 16.2 | 2 | 1.24 | 3 |
| Ex. 6 | 3 layers | Formulation Thickness (mm) | Form. 1 / 0.69 | Form. 3 / 0.80 | Form. 1 / 0.39 | 1.87 | 8.87 | 5.14 | 0.045 | 3 | 0.53 | 3 | 0.53 | 16.6 | 3 | 3.50 | 3 |
| Ex. 7 | 3 layers | Formulation Thickness (mm) | Form. 2 / 0.89 | Form. 4 / 0.69 | Form. 2 / 0.47 | 2.05 | 8.41 | 4.31 | 0.067 | 2 | 0.77 | 2 | 0.79 | 17.7 | 2 | 0.25 | 4 |
| Ex. 8 | 3 layers | Formulation Thickness (mm) | Form. 2 / 0.64 | Form. 4 / 0.57 | Form. 2 / 0.67 | 1.88 | 7.62 | 3.87 | 0.262 | 2 | 0.78 | 2 | 0.84 | 15.8 | 2 | 1.32 | 3 |
| Ex. 9 | 3 layers | Formulation Thickness (mm) | Form. 2 / 0.72 | Form. 4 / 0.73 | Form. 2 / 0.75 | 2.20 | 8.43 | 4.04 | 0.063 | 2 | 0.73 | 2 | 0.89 | 15.6 | 2 | 1.88 | 3 |
| Ex. 10 | 3 layers | Formulation Thickness (mm) | Form. 1 / 0.66 | Form. 4 / 0.84 | Form. 1 / 9.40 | 1.90 | 8.97 | 5.17 | 0.066 | 2 | 0.77 | 2 | 1.15 | 20.7 | 2 | 7.07 | 2 |
| Comp. Ex 1 | 3 layers | Formulation Thickness (mm) | Form. 2 / 0.29 | Form. 1 / 2.15 | Form. 2 / 0.26 | 2.70 | 6.92 | 1.52 | 0.159 | 1 | 1.52 | 1 | 1.83 | 15.5 | 1 | 0.02 | 4 |
| Comp. Ex. 2 | 1 layer | Formulation Thickness (mm) | | Form. 1 / — | | 2.00 | 8.00 | 4.00 | 0.163 | 1 | 1.78 | 1 | 2.59 | 12.3 | 1 | 1.03 | 3 |
| Comp. Ex. 3 | 1 layer | Formulation Thickness (mm) | | Form. 2 / — | | 2.00 | 8.00 | 4.00 | 0.187 | 1 | 1.93 | 1 | 2.77 | 13.6 | 1 | 0.05 | 4 |
| Comp. Ex 4 | 1 layer | Formulation Thickness (mm) | | Form. 3 / — | | 2.0 | 8.0 | 4.0 | 0.023 | 4 | 0.11 | 4 | 0.28 | 20.5 | 4 | 35.4 | 1 |
| Comp. Ex 5 | 1 layer | Formulation Thickness (mm) | | Form. 4 / — | | 2.0 | 8.0 | 4.2 | 0.326 | 4 | 0.11 | 4 | 2.27 | 22.3 | 4 | 20.1 | 1 |

TABLE 2-continued

| | Layer Config. | | Inner Layer Thickness (mm) | Interm. Layer | | Outer Layer | Dimensions | | | Thread Passability | | Needle Passability | | Sensation of Needle Piercing and Insertion | | | Liquid Leakage Preventability | |
|---|---|---|---|---|---|---|---|---|---|---|---|---|---|---|---|---|---|---|
| | | | | | | | Thickness (mm) | Outer Diameter (mm) | Inner Diameter (mm) | Resistance (N) | Eval | Resistance (N) | Eval | Intensity (N) | Displacement (mm) | Eval | Leakage (mL) | Eval |
| Comp. Ex. 6 | 1 layer | Thickness (mm) | | silicone | | | 2.0 | 8.0 | 4.0 | 0.119 | 1 | 1.20 | 1 | 1.57 | 8.31 | 1 | 40.4 | 1 |
| Comp. Ex. 7 | 1 layer | Thickness (mm) | | polyurethane | | | 2.0 | 8.0 | 4.0 | 0.152 | 1 | 1.53 | 1 | 1.93 | 15.32 | 1 | 29.8 | 1 |
| Comp. Ex. 8 | 3 layers | Thickness (mm) | 0.71 | natural rubber | 0.51 | 0.42 | 1.64 | 7.43 | 4.14 | 0.189 | 1 | 1.78 | 1 | 2.73 | 11.9 | 1 | 0.06 | 4 |
| Ref. Ex. 1 | 3 layers | Thickness (mm) | 0.15 | porcine aorta | 1.50 | 0.10 | 1.75 | 20.5 | 17.0 | 0.242 | 3 | 0.76 | 2 | 2.88 | 3.29 | 2 | 9.15 | 2 |
| Ref. Ex. 2 | 3 layers | Thickness (mm) | 0.02 | procine vena cava | 0.46 | 0.02 | 0.50 | 10.9 | 9.9 | 0.010 | 4 | 0.55 | 3 | 0.68 | 4.89 | 2 | 9.53 | 2 |
| Ref. Ex. 3 | 3 layers | Thickness (mm) | 0.04 | porcine carotid | 0.75 | 0.04 | 0.83 | 6.4 | 4.7 | 0.039 | 3 | 0.41 | 3 | 0.54 | 5.16 | 3 | 9.97 | 2 |

As shown in Table 1, the artificial blood vessels of the examples provide a sensation of needle insertion upon puncturing and a needle thread passability resembling those of blood vessels of animals including humans, as well as high liquid leakage preventability. In contrast, the results show that the artificial blood vessels of the comparative examples could not achieve a sensation of needle insertion upon puncturing and a needle thread passability together with high liquid leakage preventability.

The invention claimed is:

1. An artificial blood vessel comprising:
a first layer formed using a resin composition I, the resin composition I comprising:
100 parts by mass of a component (A) hydrogenated block copolymer;
300 parts by mass or more and 1000 parts by mass or less of a component (B) oil; and
0.1 parts by mass or more and 150 parts by mass or less of a component (C) lubricant;
a second layer formed on an exterior of the first layer using a resin composition II, the resin composition II being free of the component (C) lubricant and comprising:
100 parts by mass of the component (A) hydrogenated block copolymer; and
50 parts by mass or more and 1000 parts by mass or less of the component (B) oil; and
a third layer formed on an interior of the first layer using a resin composition III, the resin composition III being free of the component (C) lubricant and comprising:
100 parts by mass of the component (A) hydrogenated block copolymer; and
50 parts by mass or more and 1000 parts by mass or less of the component (B) oil,
wherein:
the component (A) hydrogenated block copolymer contains one or more hydrogenated products of an aromatic vinyl-conjugated diene block copolymer containing a block unit derived from an aromatic vinyl and a block unit derived from a conjugated diene, and
a content of the block unit derived from an aromatic vinyl in the aromatic vinyl-conjugated diene block copolymer is 5 mass % or more and 50 mass % or less.

2. The artificial blood vessel according to claim 1, wherein the artificial blood vessel is tubular.

3. The artificial blood vessel according to claim 1, wherein the artificial blood vessel has a first peak load value of 0.01 N or more and 1.2 N or less upon needle penetration by puncturing at a speed of 1000 mm/min. under a condition of 23° C.±1° C. using a universal testing machine.

4. The artificial blood vessel according to claim 1, wherein the artificial blood vessel has a load value of 0.1 N or more and 1 N or less applied on a puncture needle and/or a load value of 0.01 N or more and 0.1 N or less applied on a medical thread, when punctured at a speed of 1000 mm/min. using a universal testing machine provided with a puncture needle and a medical thread.

5. The artificial blood vessel according to claim 1, wherein the artificial blood vessel, after being punctured 50 times with an injection needle, has a liquid leakage amount of 10 mL or less in 60 sec. under a pressure of 60 mmHg.

6. The artificial blood vessel according to claim 1, wherein the component (C) lubricant comprises at least one lubricant selected from the group consisting of an ionic surfactant and a nonionic surfactant.

7. The artificial blood vessel according to claim 1, wherein the component (A) hydrogenated block copolymer has a MFR (temperature 230° C., load 2.16 kg) of 1 g/10 min. or less.

8. The artificial blood vessel according to claim 1, wherein the component (B) oil has a kinematic viscosity of 0.1-100 mm$^2$/s at 37.8° C. or 40° C.

9. The artificial blood vessel according to claim 1, wherein the component (B) oil has a kinematic viscosity of 0.1-15 mm$^2$/s at 37.8° C. or 40° C.

10. The artificial blood vessel according to claim 1, wherein the content of the block unit derived from an aromatic vinyl in the aromatic vinyl-conjugated diene block copolymer is 20 mass % or more and 40 mass % or less.

* * * * *